United States Patent
Zaid et al.

(10) Patent No.: US 11,576,902 B2
(45) Date of Patent: Feb. 14, 2023

(54) INHIBITION OF COVID-19 VIRUS

(71) Applicant: Ankh Life Sciences Limited, Dublin (IE)

(72) Inventors: Gene H. Zaid, Hutchinson, KS (US); Robert Preston Moore, Great Bend, KS (US); Cameron E. West, Sterling, KS (US); Jason H. West, Hutchinson, KS (US); Krishna Mohan Donavalli, Wichita, KS (US)

(73) Assignee: Ankh Life Sciences Limited, Dublin (IE)

( * ) Notice: Subject to any disclaimer, the term of this patent is extended or adjusted under 35 U.S.C. 154(b) by 155 days.

(21) Appl. No.: 17/108,851

(22) Filed: Dec. 1, 2020

(65) Prior Publication Data
US 2022/0168282 A1   Jun. 2, 2022

(51) Int. Cl.
*A61K 31/437* (2006.01)
*A61K 9/00* (2006.01)
*A61P 31/14* (2006.01)

(52) U.S. Cl.
CPC .......... *A61K 31/437* (2013.01); *A61K 9/0019* (2013.01); *A61P 31/14* (2018.01)

(58) Field of Classification Search
CPC ................ A61K 31/437; A61P 31/14
See application file for complete search history.

(56) References Cited

U.S. PATENT DOCUMENTS 10,947,253 B2 *   3/2021   Blagg .................. C07D 215/06
2021/0040121 A1   2/2021   Blagg et al.

OTHER PUBLICATIONS

Huynh, Tien et al. "In Silico Exploration of the molecular Mechanism of Clinically Oriented Drugs for Possibly Inhibiting SARS-CoV-2's Main Protease." J.Phys.Chem.Lett. 2020, 11, 4413-4420.
Sharma, Shilpa et al. "In-Silico Drug Repurposing for Targeting SARS-CoV-2 Mpro." ChemRxiv. Preprint, https://doi.org/10.26434/chemrxiv.12210845.v1 (2020).

* cited by examiner

*Primary Examiner* — Shengjun Wang
(74) *Attorney, Agent, or Firm* — Hovey Williams LLP

(57) ABSTRACT

The treatment of human subjects suffering from COVID-19 comprises the step of administering to the human subjects a medicament selected from the group consisting of 1,3-bis (7-methoxy-4,9-dihydro-3H-pyrido[3,4-b]indol-1-yl)propane, and/or the isomers, tautomers, enantiomers, esters, derivatives, metal complexes, prodrugs, solvates, metabolites, and pharmaceutically acceptable salts thereof. The medicament may also be contacted with SARS-CoV-2 virus for inhibition of the virus.

8 Claims, 6 Drawing Sheets

Specification includes a Sequence Listing.

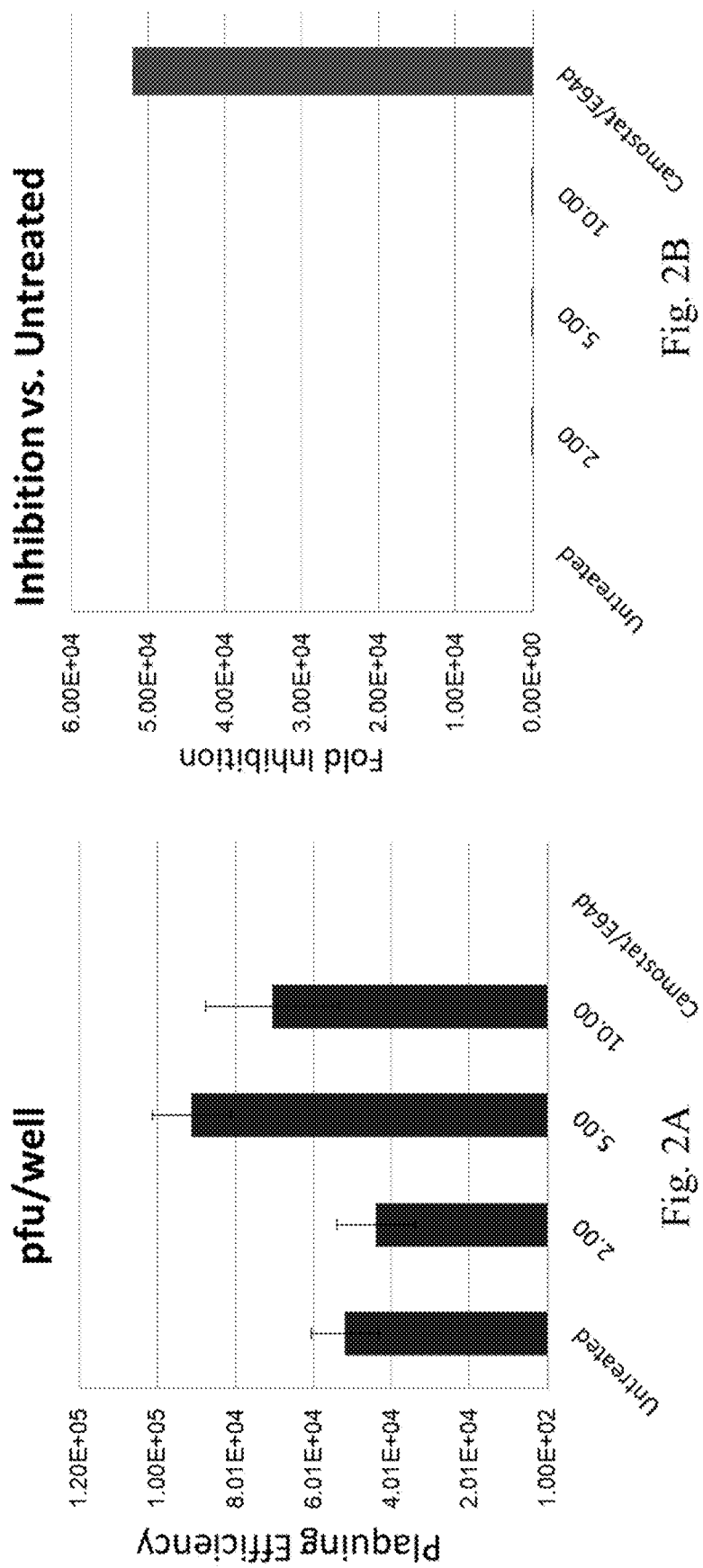

INHIBITION OF COVID-19 VIRUS

SEQUENCE LISTING

The following application contains a sequence listing in computer readable format (CRF), submitted as a text file in ASCII format entitled "Sequence Listing_53911-US" created on Nov. 30, 2020, as 15 KB. The content of the CRF is hereby incorporated by reference.

BACKGROUND OF THE INVENTION

Field of the Invention

The present invention is broadly concerned with a new medicament for the treatment of SARS-CoV-2 virus, the cause of the ongoing COVID-19 pandemic. More particularly, the invention is concerned with the use of 1,3-bis(7-methoxy-4,9-dihydro-3H-pyrido[3,4-b]indol-1-yl)propane, a fused bicyclic compound including two harmaline moieties bonded via a hydrocarbon linker, which is an effective agent against the virus and the resulting COVID-19 disease.

Description of the Prior Art

The COVID-19 pandemic, also known as the coronavirus pandemic, is an ongoing pandemic of coronavirus disease 2019 (COVID-19) caused by severe acute respiratory syndrome coronavirus 2 (SARS-CoV-2), first identified in December 2019 in Wuhan, China. The World Health Organization declared the outbreak a Public Health Emergency of International Concern in January 2020 and a pandemic in March 2020. As of 12 Nov. 2020, more than 52.3 million cases have been confirmed, with more than 1.28 million deaths attributed to COVID-19.

COVID-19 mainly spreads through the air when people are near each other long enough, primarily via small droplets or aerosols, as an infected person breathes, coughs, sneezes, sings, or speaks. Transmission via fomites (contaminated surfaces) has not been conclusively demonstrated. It can spread as early as two days before infected persons show symptoms (presymptomatic), and from asymptomatic (no symptoms) individuals. People remain infectious for up to ten days in moderate cases, and two weeks in severe cases.

Common symptoms include fever, cough, fatigue, breathing difficulties, and loss of smell and taste. Complications may include pneumonia and acute respiratory distress syndrome. The incubation period is typically around five days but may range from one to 14 days.

The responses have caused global social and economic disruption, including the largest global recession since the Great Depression. It has led to the postponement or cancellation of events, widespread supply shortages exacerbated by panic buying, famines affecting hundreds of millions of people, and decreased emissions of pollutants and greenhouse gases. Educational institutions have been partially or fully closed. Misinformation has circulated through social media and mass media.

As of November 2020, there were more than 10,200,000 confirmed cases and 239,000 COVID-19-related deaths in the US, representing nearly one-fifth of the world's known cases and deaths, and the most cases and deaths of any country.

In response to these conditions, there has been a tremendous scientific effort to develop both vaccines and medications. There are several vaccine candidates in development, although none have completed clinical trials. There is no known specific antiviral medication, so primary treatment is currently symptomatic.

There is accordingly a need in the art for new and effective treatments against COVID-19, to ameliorate the worldwide consequences of the pandemic.

SUMMARY OF THE INVENTION

It has now been discovered that a fused bicyclic compound (sometimes referred to herein as "GZ440-6"), comprising a pair of harmaline moieties linked via a $CH_2$ methine group bonded to the respective methyl substituents of the harmaline moieties, is an effective inhibitor of the SARS-CoV-2 virus. This compound, 1,3-bis(7-methoxy-4, 9-dihydro-3H-pyrido[3,4-b]indol-1-yl)propane, has the structure:

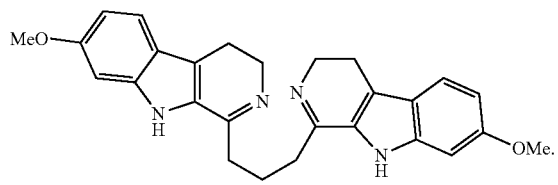

1,3-bis(7-methoxy-4,9-dihydro-3H-pyrido[3,4-b]indol-1-yl)propane
Chemical Formula: $C_{27}H_{28}N_4O_2$
Exact Mass: 440.22
Molecular Weight: 440.55

This compound and/or the isomers, tautomers, enantiomers, esters, derivatives, metal complexes, prodrugs, solvates, metabolites, and pharmaceutically acceptable salts thereof, may be administered to human subjects suffering from COVID-19 in therapeutically effective amounts in order to lessen the severity of the disease and/or its attendant symptoms and/or the duration of the disease.

The use of the compound and its variants for the treatment of human subjects suffering from COVID-19, and/or the use thereof in the manufacture of a medicament for such treatment, is also within the ambit of the invention.

Alternately, the compound or its variants may be contacted with SARS-CoV-2 virus in order to inhibit the growth, replication, and/or viability of the virus. Such usages would typically be in vitro.

BRIEF DESCRIPTION OF THE DRAWINGS

FIG. 1A illustrates a first cytotoxicity run when using the compound at 2.0 μM, 5.0 μM and 10.0 μM, where the cytotoxicity values are comparable to the 1×C/E control inhibitors;

FIG. 1B illustrates a second cytotoxicity run tested with the compound of the invention at 2.0 μM, 5.0 μM and 10.0 μM;

FIG. 1C illustrates a third cytotoxicity run tested with compound at 10 μM, 20 μM and 40 μM; and FIG. 1D illustrates average cytotoxicity values, not elevated above controls;

FIGS. 2A-2D depict representative results from independent virus plaque formation assays:

FIG. 2A illustrates the measure of the number of plaque forming units (pfu) per well for cells treated with different concentrations of the compound of the invention at 2.0, 5.0 and 10.0 µM as compared to the control;

FIG. 2B illustrates the measure of inhibitory activity relative to untreated controls;

FIG. 2C illustrates pfu per well for cells treated with increased concentrations of the compound of the invention at 10, 20 and 40 µM as compared to the control; and FIG. 2D illustrates the measure of inhibitory activity relative to untreated controls.

FIG. 3A sets forth the results of Run 1 and confirms that there is no consistent reduction of viral numbers in cells 120 hours after infection at the lower concentrations indicated;

FIG. 3B sets forth the results of Run 2 and provides further confirmation consistent with FIG. 3B; and FIG. 3C illustrates that increasing concentration of the compound of the invention resulted in a clear reduction in viral numbers using the compound of the invention at 40 µM ($P<0.05$).

DETAILED DESCRIPTION OF THE PREFERRED EMBODIMENT

Figure 1A:
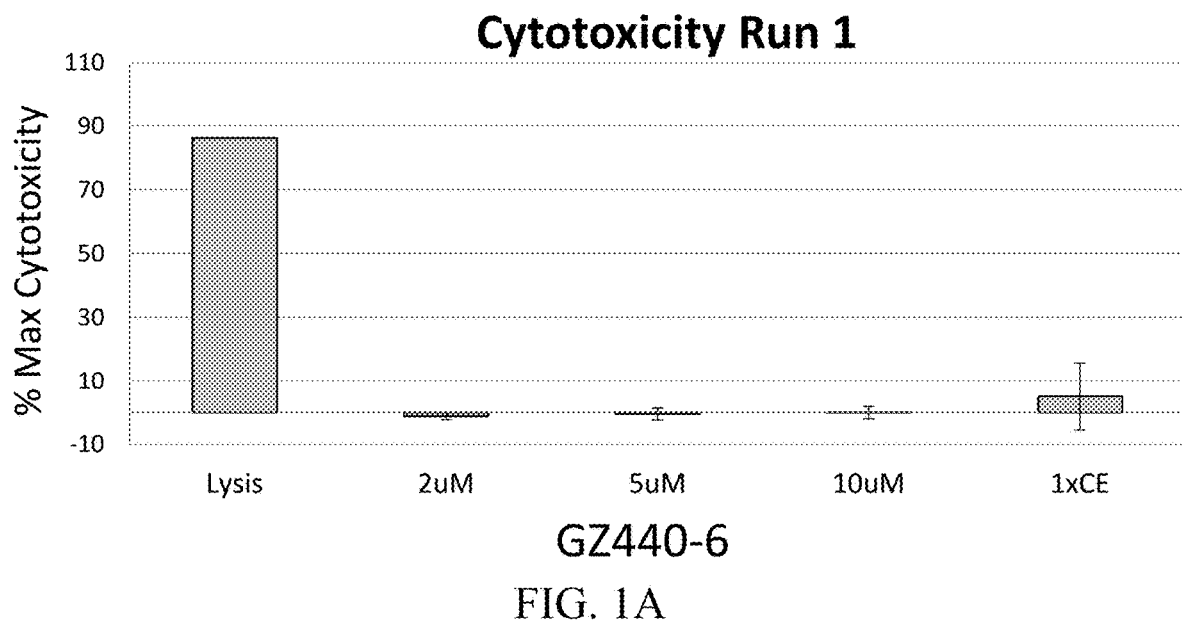
FIGS. 1A-1D depict representative results from three independent runs of the cytotoxicity assay forming a part of the Example, and average results; error bars are standard deviations. In particular.
Figure 1B:
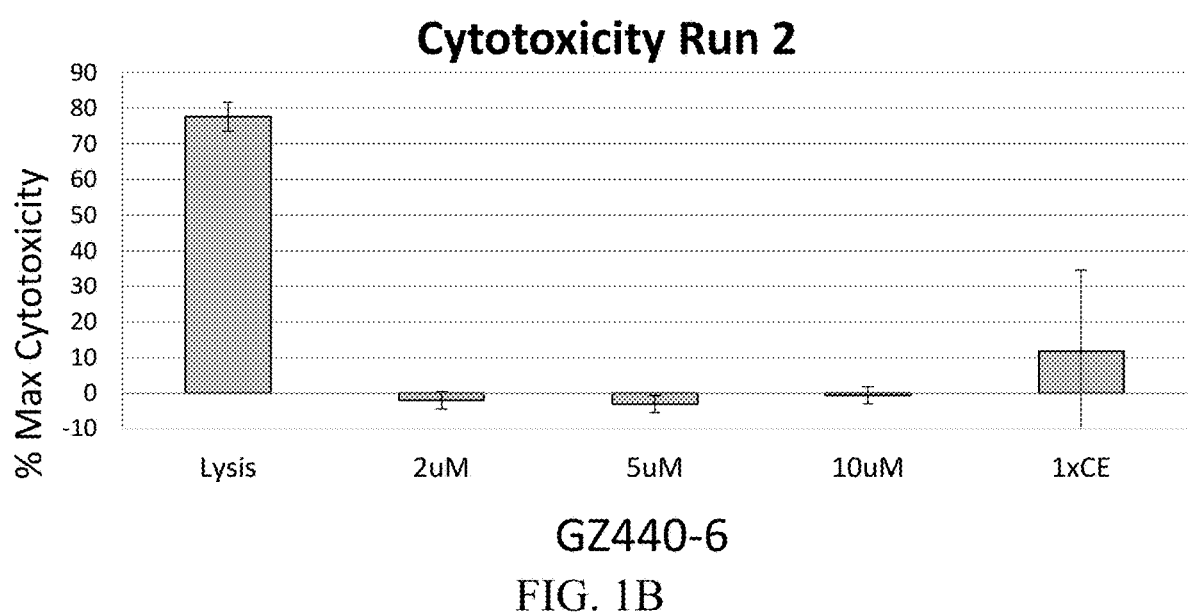

The GZ440-6 compound, among others, is described in pending U.S. application Ser. No. 16/531,601 filed Aug. 5, 2019, entitled FUSED POLYCLIC DIMERS, and the relevant portions of this application are incorporated herein by reference. That application teaches that the compound is a useful anti-cancer agent, but does not deal with or suggest any utility against the COVID-19 virus.

Methods described herein include those for inhibiting replication of coronavirus. In one aspect, the methods comprise (consist essentially or even consist of) contacting coronavirus with an amount of GZ440-6 effective to inhibit viral replication. In one aspect, the methods comprise (consist essentially or even consist of) administering a therapeutically or prophylactically effective amount of GZ440-6 to a human subject in need thereof. The subject may be at risk of viral infection or exposure to coronavirus and/or may be an individual identified as having been infected with coronavirus. Such individual may be symptomatic or asymptomatic. Thus, "therapeutic" use of the compound refers to processes that are intended to produce a beneficial change in an existing condition (e.g., viral infection) of a subject, such as by reducing the severity of the clinical symptoms and/or effects of the infection, and/or reducing the duration of the infection/symptoms/effects. Likewise, "prophylactic" use refer to processes that are intended to inhibit or ameliorate the effects of a future viral infection to which a subject may be exposed (but is not currently infected with). In some cases, the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects). In either case, the compounds are still considered to "prevent" the target infection.

More particularly, the invention relates to methods comprising (or consisting essentially of or even consisting of) the step of administering to a human subject suffering from COVID-19 the GZ440-6 compound, as well as variants such as the isomers, tautomers, enantiomers, esters, derivatives, metal complexes (e.g., Cu, Fe, Zn, Pt, V), prodrugs, solvates, metabolites, and pharmaceutically acceptable salts thereof. Reference to GZ440-6 herein thus embraces not only the compound per se, but the above variants thereof. As used herein, the term "inhibit" refers to a reduction or decrease viral titer or quantity, compared to a baseline. For example, in the context of the present invention, inhibition of viral replication refers to a decrease in amount or speed of viral replication as compared to baseline. In some embodiments there is a reduction of at least about 30%, about 40%, about 50%, about 60%, about 70%, about 75%, about 80%, about 85%, about 90%, about 95%, about 99%, and about 100%. Those of ordinary skill in the art can readily determine whether or not viral replication has been inhibited and to what extent. Thus, an "effective amount" to inhibit viral replication refers to the amount of GZ440-6 that results in a reduced level of viral replication and thus a reduced amount of detectable virus in the individual (e.g., reduced viral titer or viral load). Correspondingly, such reductions in viral load will advantageously lead to an amelioration, improvement, or decrease in one or more symptoms associated with coronavirus infection and/or reduced transmission of the virus from the infected individual. Assays for viral replication also provide one with the ability to determine the efficacy of viral inhibitors and are well known to those skilled in the art, and are demonstrated in the Examples. Such assays may be conducted in vivo or in vitro.

"Isomers" refers to each of two or more compounds with the same formula but with at different arrangement of atoms, and includes structural isomers and stereoisomers (e.g., geometric isomers and enantiomers); "tautomers" refers to two or more isometric compounds that exist in equilibrium, such as keto-enol and imine and enamine tautomers; "derivatives" refers to compounds that can be imagined to arise or actually be synthesized from a defined parent compound by replacement of one atom with another atom or a group of atoms; "solvates" refers to interaction with a defined compound with a solvent to form a stabilized solute species; "metabolites" refers to a defined compound which has been metabolized in vivo by digestion or other bodily chemical processes; and "prodrugs" refers to defined compound which has been generated by a metabolic process. The compounds can be directly used in partial or essentially completely purified forms, or can be modified as indicated above. The compounds may be in crystalline or amorphous forms, and may be lyophilized.

"Pharmaceutically acceptable salts" with reference to the components means salts of the components which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts Properties, and Use, P. H. Stahl & C. G. Wermuth eds., ISBN 978-3-90639-058-1 (2008).

GZ440-6 as administered should be of high purity, e.g., at least about 95% (more preferably at least about 99%) pure. Inasmuch as the compound is synthesized, purity levels can be controlled. Antiviral compositions comprising (consisting essentially or even consisting of) GZ440-6 are also contemplated. The compositions may include additional inactive pharmaceutically-acceptable ingredients and/or vehicles as a base carrier composition in which the active ingredients are dispersed. As used herein, the term "pharmaceutically-acceptable" means not biologically or otherwise undesirable, in that it can be administered to a subject without excessive toxicity, irritation, or allergic response, and does not cause any undesirable biological effects or interact in a deleterious manner with any of the other components of the composition in which it is contained. The term "carrier," as used herein, means one or more compatible base compositions with which the active ingredient (e.g., GZ440-6) is combined to facilitate the administration of ingredient, and which is suitable for administration to a patient. Such preparations may also routinely contain salts, buffering agents, preservatives, and optionally other therapeutic ingredients or adjuvants. The carrier would naturally be selected to minimize any degradation of the active ingredient and to minimize any adverse side effects in the subject, as would be well known to one of ordinary skill in the art. Pharmaceutically-acceptable ingredients include those acceptable for veterinary use as well as human pharmaceutical use. The term "adjuvant" is used herein to refer to substances that have immunopotentiating effects and are added to or co-formulated in a therapeutic composition in order to enhance, elicit, and/or modulate the innate, humoral, and/or cell-mediated immune response against the active ingredients.

The GZ440-6 may be administered to a human subject in any convenient manner, such as by oral, rectal, nasal, ophthalmic, parenteral (including intraperitoneal, gastrointestinal, intrathecal, intravenous, cutaneous (e.g., dermal patch), subcutaneous (e.g. injection or implant), or intramuscular) administrations. The dosage forms of the invention may be in the form of liquids, gels, suspensions, solutions, or solids (e.g., tablets, pills, or capsules). Moreover, therapeutically effective amounts of the agents of the invention may be co-administered with other antiviral agent(s), where the two products are administered substantially simultaneously or in any sequential manner. It is presently believed that oral administration is the preferred route.

Levels of dosing to human subjects of GZ440-6 are quite variable owing to factors such as the patient's age, patient's physical condition, and the severity of the disease. In general, however, regardless of the dosage form or route of administration employed, the compositions should be dosed of from about 5 to 2000 mg per day, and more usually from about 100-800 mg per day. Such dosages may be based on a single administration per day, but more usually multiple administrations per day.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLE

The following example sets forth methods in accordance with the invention. It is to be understood, however, that this example is provided by way of illustration and nothing therein should be taken as a limitation upon the overall scope of the invention.

In Vitro Assay of COVID 19 Using GZ440-6

The antiviral activity of a diharmaline compound, designated as GZ440-6, at different concentrations (2 µM, 5 µM, 10 µM, 20 µM and 40 µM) on coronaviruses was assessed in vitro using novel coronavirus SARS-CoV-2 isolate USA-WA1/2020 (deposited by the Centers for Disease Control and Prevention and obtained through BEI Resources, NIAID, NIH: SARS-Related Coronavirus 2, Isolate USA-WA1/2020, NR-52281) and human coronavirus strain HCoV_NL63 (obtained through BEI Resources, NIAID, NIH: Human Coronavirus, NL63, NR-470).

For propagation and experimentation with SARS-CoV-2, we used Vero E6 (ATCC® CRL-1586™) and Calu-3 cells (ATCC® HTB-55™) purchased from the American Type Culture Collection (ATCC, Manassas, Va., USA) and maintained in EMEM (Eagle's Minimum Essential Medium) cell culture media (cat #30-2003, ATCC, Manassas, Va., USA) supplemented with 2% or 10% fetal bovine serum (FBS), 100 U/mL penicillin, 100 µg/mL streptomycin, 0.01M HEPES buffer solution, 1 mM sodium pyruvate, 1× non-essential amino acids solution (cat #SH3023801, Thermo Fisher Scientific, Waltham, Mass., USA), and 2 mM L-glutamine. For the propagation and experimentation with the NL63 coronavirus, we use LLC-MK2 cells (ATCC® CCL-7™) maintained in Medium 199 (cat #M4530, Millipore Sigma, St. Louis, Mo., USA) supplemented with 2% or 10% FBS, 100 U/mL penicillin, and 100 µg/mL streptomycin.

Inhibition of viral replication was assessed using reverse-transcription quantitative real-time PCR (RT-qPCR) to measure the number of virions released into the cellular supernatant of infected cells and virus plaque formation assays, hereafter plaque assays, which measure a reduction in plaque forming units (PFUs). Cytotoxicity was measured using Promega™ CytoTox 96™ Nonradioactive Cytotoxicity Assay (cat #G1780, Promega, Madison, Wis., USA).

A. Plaque Assays—Viral Titers 6-well plates (cat #CLS3516, Millipore Sigma, St. Louis, Mo., USA) were seeded with ~3.0×10^5 cells/well. Vero E6 and LLC-MK2 cells were incubated for 48-72 hours at 37° C. in 5% CO2 atmosphere until 80-90% confluency was achieved, while Calu-3 cells were incubated for >10 days to achieve 80-90% confluency. Prior to infection the 10% FBS containing growth media was replaced with fresh media containing 2% FBS supplemented with varying concentrations of GZ440-6 (as appropriate for each experiment (see results) and infected with coronavirus (SARS-CoV-2 or NL63) at an MOI of 0.013 for SARs-CoV-2 and 0.003 for NL63 and incubated at 37° C. for 1 hour. The virus and GZ440-6 containing media was then replaced with a 1×DMEM (cat #D2902, Millipore Sigma, St. Louis, Mo., USA) agarose overlay containing the appropriate drug concentrations (10 um, 20 um and 40 µM) for each experiment, left to solidify at room temperature for 15 minutes, and incubated for 5 days at 37 C in 5% CO2 atmosphere. Combined camostat mesylate and E64d, hereafter "C/E", was used as an inhibition control for all experiments (Zhan, 2020; Targeting the entry step of SARS-CoV-2: a promising therapeutic approach) and all SARS-CoV-2 processes were conducted in a biosafety level 3 facility.

After the 5-day incubation, 2 ml of 4% paraformaldehyde was added to each overlay and left to incubate for 30 minutes at room temperature to fix the cells and inactivate the virus. The cells were then stained with 1% crystal violet, the overlay was removed, and the cells were washed 3× with PBS. Plaque forming units for each treatment group were counted, averaged, and normalized to the untreated control group. Each experimental run contained three biological replicates and each experiment was conducted a minimum of two times. Standard deviation was calculated using the variation of averaged counts among all runs. Values were plotted using GraphPad Prism version 8.0.0 for Windows (GraphPad Software, San Diego, Calif., USA) and annotations were added using Adobe Illustrator (Adobe Systems Incorporated, San Jose, Calif., USA).

B. Real-Time (RT)-qPCR

Infection and viral RNA extraction 12-well plates (cat #CLS3513, Millipore Sigma, St. Louis, Mo., USA) were seeded with ~1.0×10^5 cells/well. Vero E6 and LLC-MK2 cells were incubated for 48-72 hours at 37° C. in 5% CO2 atmosphere until 80-90% confluency was achieved, while Calu-3 cells were incubated for >10 days to achieve 80-90% confluency. Prior to infection, the growth media was replaced with fresh media containing 2% FBS supplemented with varying concentrations of GZ440-6 as appropriate for each experiment (see results) and infected with coronavirus (SARS-CoV-2 or NL63) at an MOI of 0.04 for SARs-CoV-2 and 0.01 for NL63 and incubated for up to 5 days at 37° C. in 5% CO2 atmosphere. 1× Camostat/E64D was used as an inhibition control for all experiments and all SARS-CoV-2 processes were conducted in a biosafety lab level 3 facility. Each experimental run contained two biological replicates and each experiment was conducted a minimum of two times. 400 µL of supernatant was harvested at 48 hours for SARS-CoV-2 but 5 days for NL63 and RNA was extracted using Invitrogen Pure-Link RNA kits (Thermo Fisher Scientific, Waltham, Mass., USA) following the manufacturer's recommendations for liquid extractions.

qPCR Assay Design

Two TaqMan qPCR assays were designed to target and amplify either the SARS-CoV-2 or the NL63 coronavirus. The SARS-CoV-2 qPCR amplified a 125 bp region of the spike protein (GenBank Gene ID: 43740568) using forward primer CoV2-S_19F (5'-GCTGAACATGTCAACAACTC-3' (SEQ ID NO:1)) and reverse primer CoV2-S_143R (5'-GCAATGATGGATTGACTAGC-3'(SEQ ID NO:2)) with MGB TaqMan probe CoV2-S_93FP (5'-ACTAAT-TCTCCTCGGCGGGC-3'(SEQ ID NO:3)) labelled fluorescently with a FAM dye, which was designed based off the SARS-CoV-2 genome GCF_009858895.2 (GenBank Sequence ID: MN908947.3), while the NL63 qPCR amplified a 201 bp region of membrane protein (GenBank Gene ID: YP_003770.1) using forward primer NL63_10F (5'-TGGTCGCTCTGTTAATGAAA-3'(SEQ ID NO:4)) and reverse primer NL63_200R (5'-AAAT-TTCTTCCTAGCAGCTC-3'(SEQ ID NO:5)) with MGB TaqMan probe NL63102RP (5'-CCCTCCT-GAGAGGCAACACC-3'(SEQ ID NO:6)) fluorescently labelled with a VIC dye, which was based off the HCoV_NL63 genome (GenBank Sequence ID: MN306040.1).

Reverse Transcription and PCR Amplification

Two approaches were used over the course of this study for the reverse transcription of RNA into cDNA followed by qPCR. For the first approach we used a two-step method where viral RNA was converted into cDNA using Invitrogen SuperScript IV VILO Master Mix (cat #11766500, Thermo Fisher Scientific, Waltham, Mass., USA) in 96-well format according to the manufacturer's recommendations and deactivated using 1 µL of Invitrogen RNase H (cat #18021-014, Thermo Fisher Scientific, Waltham, Mass., USA); these processes used a SimpliAmp® thermocycler (Applied Biosystems, Foster City, Calif., USA). 1 µL of template cDNA was then subjected to qPCR in 10 µL reactions containing 1×TaqMan Universal Master Mix II (w/o AmpERASE UNG) (Applied Biosystems, Foster City, Calif., USA), with 0.2 µM of each forward and reverse primer and 0.1p M of probe for the SARS-CoV-2 qPCR and 0.25 µM of each forward and reverse primer and 0.125 µM of probe for the NL63 qPCR, and thermocycled in triplicate reactions using either a QuantStudio 7 flex or QuantStudio 12K (Applied Biosystems, Foster City, Calif., USA) under the following conditions: 10 minutes at 95° C., proceeded by 40 cycles of 95° C. for 15 seconds and 60° C. for 1 minute. The second approach employed a one-step procedure in which viral RNA was converted to cDNA using the TaqMan amplification primers, immediately followed by qPCR. For this approach we used the 4× Reliance One-Step Multiplex RT-qPCR Supermix (cat #12010220, BioRad, Hercules, Calif., USA) with the same TaqMan primers, probes, and concentrations as described above for the two-step approach; however, these reactions were conducted in 20 µL volumes, instead of 10 µL. Triplicate reactions were thermocycled using the same QuantStudio instruments described previously under the following conditions: 50° C. for 10 minutes to reverse transcribe the viral RNA into cDNA, followed by 95° C. for 10 minutes, proceeded by 40 cycles of 95° C. for 10 seconds and 60° C. for 30 sec. Positive amplification and non-template controls were included on every run.

Data Analysis

A synthetic double stranded DNA fragment was generated (gBlocks Gene Fragments, Integrated DNA Technologies, Coralville, Iowa, USA) as a qPCR control that contained the amplification primers and internal gene sequence for both the SARS-CoV-2 and the NL63 target genes (see qPCR assay design section), of which copy number was known. By making a serial dilution of this control oligo from $10^8$ (undiluted) to $10^{-1}$ copies and including it on every run, we were able to extrapolate viral copy number in each of the experimental samples. Based on the inclusion of this pre-defined synthetic gBlock standard the QuantStudio instrument software generated a standard curve for each run that was used to quantify the unknown sample reactions. The calculated quantities for triplicate reactions for each sample were averaged and the standard deviation was calculated among reactions. We performed a t-test to calculate the statistical significance of each experimental value compared to the untreated control group (data not shown). Values for the experimental replicates and the standard deviations among experimental runs were averaged and then normalized to the untreated control group to obtain percent inhibition values. These values were plotted using GraphPad Prism version 8.0.0 for Windows (GraphPad Software, San Diego, Calif., USA) and annotations were added using Adobe Illustrator (Adobe Systems Incorporated, San Jose, Calif., USA).

C. Cytotoxicity

Cytotoxicity was measured using the Promega™ CytoTox 96™ Nonradioactive Cytotoxicity Assay kit (cat #G1780, Promega, Madison, Wis., USA) in 50 μL reactions and 96-well format (cat #161093, Thermo Fisher Scientific, Waltham, Mass., USA) according to the manufacturer's protocol, except we used 20 μL of 10× Lysis Solution per 100 μL of sample and incubated at 37° C. for 30 minutes to generate the maximum LDH release control. The assay was measured using a BioTeK Synergy™ HT plate reader (model #7091000, BioTek, Winooski, Vt., USA) at an optical density of 490 nm ($OD_{490}$). Cytotoxicity was measured for ≤60 μM Cmpd. x for all three cell lines (LLC-MK2, Vero E6, and Calu-3). LLC-MK2 cells were assessed for cytotoxicity at 5 days, whereas Vero E6 and Calu-3 cells were assessed for cytotoxicity every 24 hours from 1-5 days. Percent cytotoxicity was calculated by dividing the experimental LDH release at $OD_{490}$ b.

D. Results

Cytotoxicity Assay

Figure 1C:
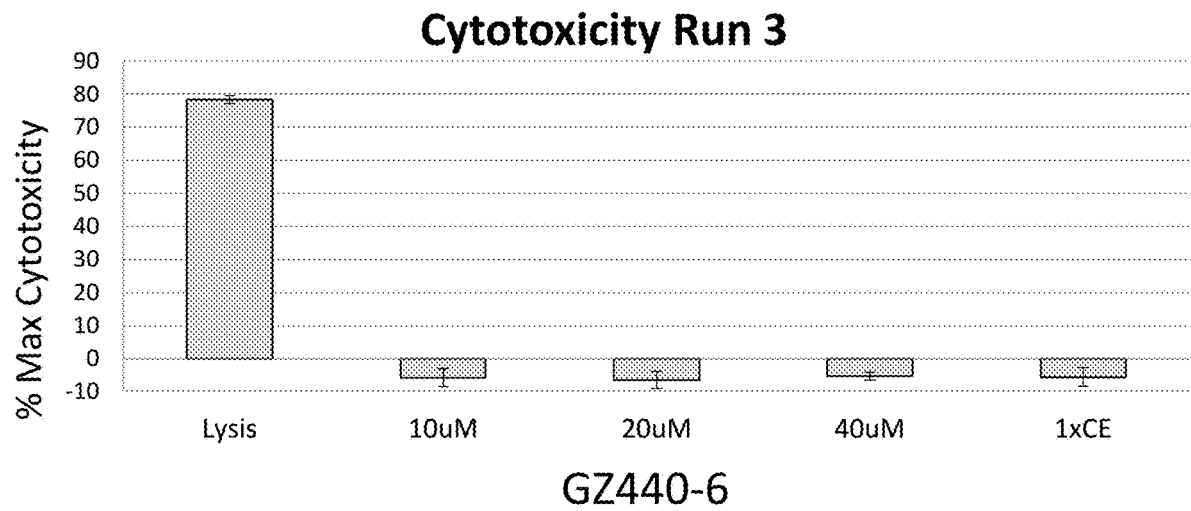
Figure 1D:
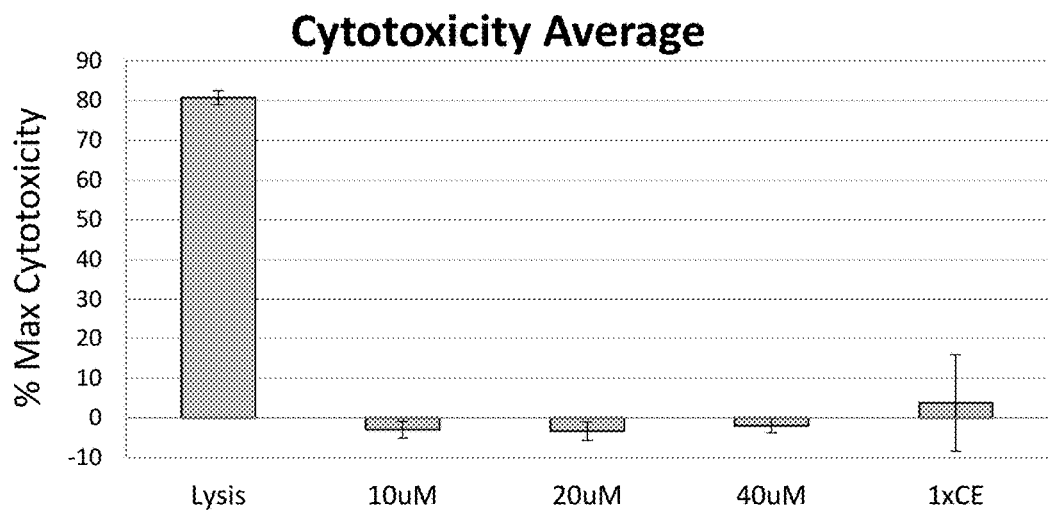

There is no significant cytotoxicity in both lower (2, 5 and 10 uM) and higher doses (20 and 40 μM) of GZ440-6 as shown in FIGS. 1A, 1B, 1C, and 1D, indicating GZ404-6 is not toxic to cells. There was negligible cytotoxicity observed in Vero-E6 cells treated with 440-6 at 2.0 μM, 5.0 μM and 10.0 μM (FIGS. 1A and 1). There was also no significant cytotoxicity the compound was administered at 20 μM and 40 μM (FIG. 1C). (Student's T-Test results 440-6 vs. Camostat/E64d P<0.05).

Virus Plaque Formation Assay

The virus plaque formation assay measures the efficiency of virus intercellular spread and induction of the cytopathic effect. This experiment uses live virus to infect mammalian cells. Virus was diluted to ~500 plaque forming units/mL with growth medium (EMEM+2.0% Fetal Bovine Serum (FBS)). Cells were infected with virus for 1 hr. at 37° C., washed once with balanced salts solution, and fresh medium containing 2.0% FBS added. The cells were observed for the formation of cytopathic effects (CPE) and plaques (clear regions in cell monolayer caused by cell death) for 5 days. Viral RNA was also isolated for determination of virus copy number 5 days following treatment. In the typical intracellular lifecycle, the virus enters the cell, is uncoated (sheds its membrane), and releases nucleic acid into the cell cytoplasm. There, the virus makes copies of its genome, and packages these into new membrane vesicles which leave the cell by "budding". The new virions then infect adjacent cells and the process continues as the virus infects new cells. This hijacking of the cellular machinery causes cellular damage (the cytopathic effect), which can be visualized as a zone of dead cells (i.e. a plaque). If a compound is effective, it may inhibit entry of the virus into the cells, multiplication or spreading from cell to cell. Plaquing efficiency for an effective inhibitor will be significantly lower than those for the untreated controls and may be comparable to the inhibitor ("C/E") control. If this is not the case, then the compound does not inhibit the lifecycle of the virus under these conditions.

Figures 2C, 2D:
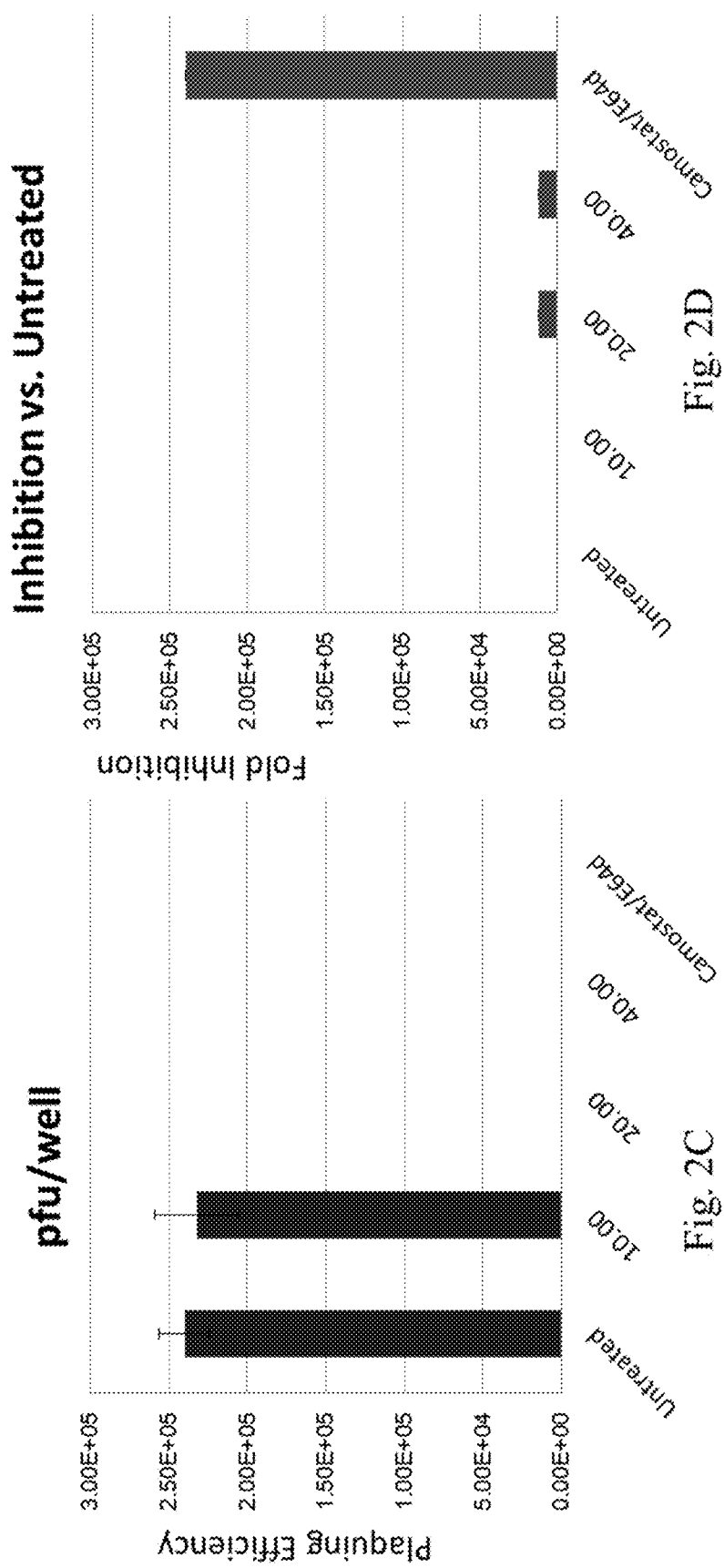

The assay was performed three times. Two representative charts are shown in FIG. 2A-2D. The results from the virus plaque formation assay using 440-6 at 2.0, 5.0 and 10.0 μM demonstrated negligible inhibition (FIG. 2A-2B). In FIG. 2A, the y-axis is a measure of the number of plaques of virus across each of the three treatment groups and two controls vs. untreated cells. Virus was diluted 100-200 plaque forming units (pfu) per well. FIG. 2B shows a measure of inhibitory activity relative to untreated controls. This is another way to look at the data. The Y axis is the degree of inhibition (measured in fold-differences) vs. untreated cells. Error bars are the standard deviation. In the presence of 440-6 at 2.0 μM, 5.0 μM and 10.0 μM, there was negligible inhibition in CoV-2 in Vero-E6 cells at 120 h after infection. However, at 20 μM and above, inhibition of plaque formation was significant (Student's T-Test results 440-6 vs. Camostat/E64d P<0.05) as shown in FIG. 2C-2D.

RT-PCR Assay

Figure 3A:
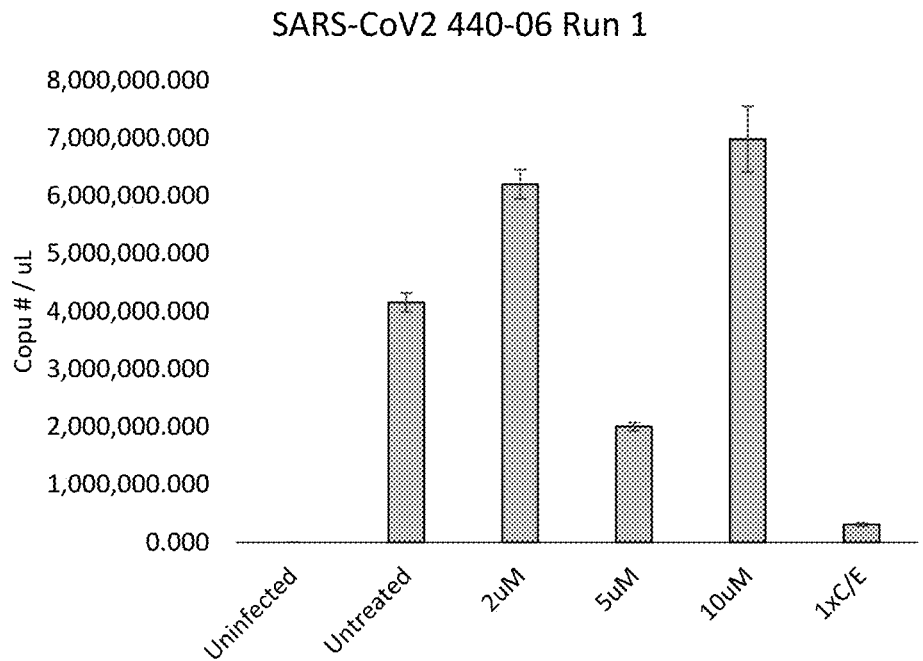
FIGS. 3A-3C illustrate viral loads (viral copy number) by RNA measurements as determined by RT-PCR. The y-axis is the average copy number of RNA molecules per microliter across three technical replicates. The x-axis lists the three controls and three treatment groups. The error bars are the standard deviations.
Figure 3B:
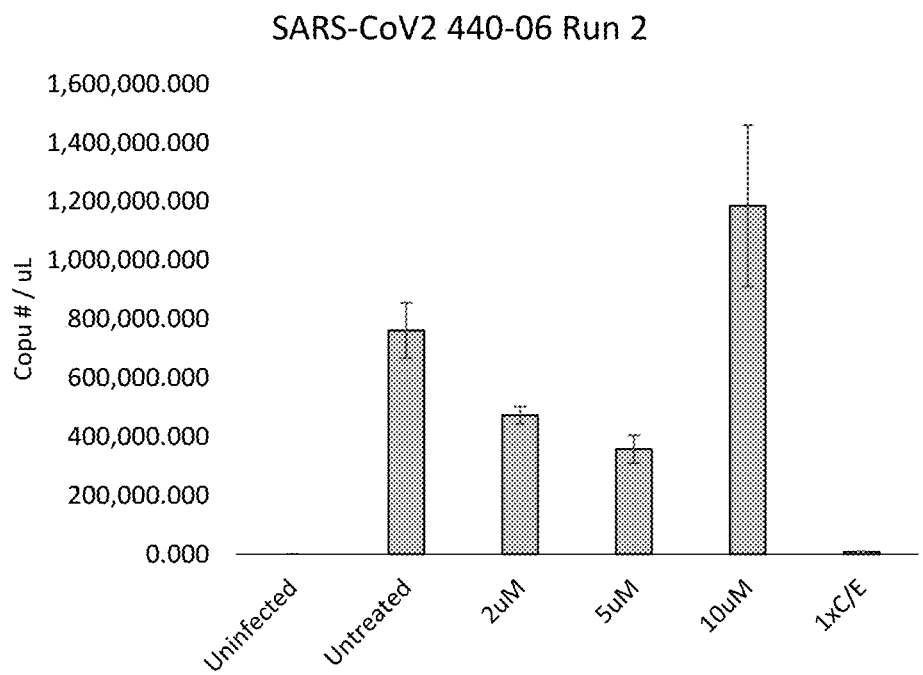
Figure 3C:
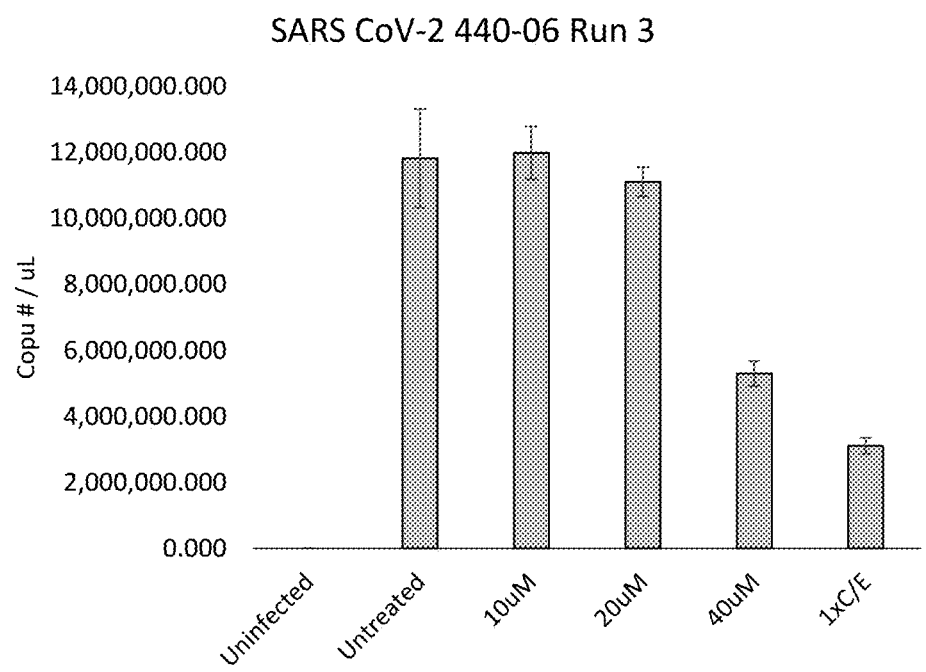

In parallel with the virus plaque formation assay, viral RNA was extracted from the cell supernatants at 5 days after infection with SARS-CoV-2. RNA levels indicate the number of copies of the virus measured by reverse transcription-polymerase chain reaction, or RT-PCR. If the treatment is inhibitory, RNA levels will be significantly lower in the treated vs. the untreated control. If treatment is not inhibitory, then the RNA copy number will be more comparable to the untreated controls. Viral RNA extractions were assayed in duplicate for each treatment per run of the virus plaque formation assay. The experiment was performed at least 3 times. Overall, the RT-PCR assay has a greater range of detection and sensitivity compared to the plaque assay above (FIGS. 2A-2D). Quantitation of viral copy number by RNA measurements indicated consistent reduction of viral numbers in cells 120 hours after viral infection to cells. Treatment of GZ440-6 at higher concentrations (20 and 40 μM) decreased viral load indicating reduction of viral RNA levels in higher concentrations, but not in lower concentrations as shown in FIG. 3A-C. These results are consistent with plaque formation as demonstrated in FIG. 2A-D.

We claim:

1. A method of inhibiting viral replication in a human subject exposed to or at risk of exposure to SARS-CoV-2 virus, or suffering from COVID-19, comprising the step of administering to the subject a prophylactically or therapeutically effective amount of a medicament selected from the group consisting of 1,3-bis(7-methoxy-4,9-dihydro-3H-pyrido[3,4-b]indol-1-yl)propane, and/or the isomers, tautomers, enantiomers, esters, derivatives, metal complexes, prodrugs, solvates, metabolites, and pharmaceutically acceptable salts thereof, which said medicament inhibits replication of said SARS-CoV-2 virus in said subject.

2. The method of claim 1, said medicament being administered to said human subject by a route selected from the group consisting of oral, rectal, nasal, ophthalmic, and parenteral administrations.

3. The method of claim 1, said medicament being administered at a level of from about 5 to 2000 mg per day.

4. The method of claim 1, wherein said human subject is suffering from one or more symptoms of COVID-19 prior to said administration step.

5. The method of claim 1, wherein said human subject is asymptomatic for COVID-19 prior to said administration step.

6. The method of claim 1, wherein said human subject has a baseline amount of detectable SARS-CoV-2 virus prior to said administration step, wherein after said administration step, said baseline amount of detectable virus is reduced by at least 30%.

7. A method of treating a human subject suffering from COVID-19, comprising the step of administering to the subject a therapeutically effective amount of a compound selected from the group consisting of 1,3-bis(7-methoxy-4,9-dihydro-3H-pyrido[3,4-b]indol-1-yl)propane, and/or the isomers, tautomers, enantiomers, esters, derivatives, metal complexes, prodrugs, solvates, metabolites, and pharmaceutically acceptable salts thereof.

8. A method of inhibiting SARS-CoV-2 viral replication, comprising the step of contacting said virus with a compound selected from the group consisting of 1,3-bis(7-methoxy-4,9-dihydro-3H-pyrido[3,4-b]indol-1-yl)propane, and/or the isomers, tautomers, enantiomers, esters, derivatives, metal complexes, prodrugs, solvates, metabolites, and pharmaceutically acceptable salts thereof.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 1
gctgaacatg tcaacaactc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 2
gcaatgatgg attgactagc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic PCR probe

<400> SEQUENCE: 3
actaattctc ctcggcgggc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 4
tggtcgctct gttaatgaaa                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 5
aaatttcttc ctagcagctc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic PCR probe

<400> SEQUENCE: 6
ccctcctgag aggcaacacc                                              20
```